United States Patent [19]

Immel et al.

[11] Patent Number: 5,248,840
[45] Date of Patent: Sep. 28, 1993

[54] PROCESS FOR THE PREPARATION OF HYDROOXYDIPHENYLS

[75] Inventors: Otto Immel; Gerhard Darsow, both of Krefeld; Udo Birkenstock, Ratingen, all of Fed. Rep. of Germany

[73] Assignee: Bayer Aktiengesellschaft, Leverkusen, Fed. Rep. of Germany

[21] Appl. No.: 950,619

[22] Filed: Sep. 24, 1992

[30] Foreign Application Priority Data

Oct. 4, 1991 [DE] Fed. Rep. of Germany ....... 4132944

[51] Int. Cl.$^5$ .................... C07C 39/12; C07C 37/00
[52] U.S. Cl. .................................................... 568/747
[58] Field of Search ................. 568/747, 748, 744

[56] References Cited

U.S. PATENT DOCUMENTS

| | | | |
|---|---|---|---|
| 4,060,559 | 11/1977 | Goto et al. | 568/747 |
| 4,080,340 | 3/1978 | Imamura | 568/747 |
| 4,729,977 | 3/1988 | Immel et al. | 502/170 |
| 4,902,661 | 2/1990 | Immel et al. | 502/184 |

FOREIGN PATENT DOCUMENTS

| | | | |
|---|---|---|---|
| 0208933 | 6/1986 | European Pat. Off. | |
| 0325132 | 7/1989 | European Pat. Off. | |
| 2211721 | 3/1972 | Fed. Rep. of Germany. | |
| 0003042 | 1/1977 | Japan | 568/747 |
| 1327581 | 8/1973 | United Kingdom | 568/747 |
| 0000987 | 2/1989 | World Int. Prop. O. | 568/747 |

Primary Examiner—Werren B. Lone
Attorney, Agent, or Firm—Sprung Horn Kramer & Woods

[57] ABSTRACT

To prepare hydroxydiphenyls, a compound or a mixture of several compounds consisting of completely or partly hydrogenated hydroxydiphenyl is dehydrogenated catalytically in the gas phase, a catalyst being employed which comprises, as the active constituents, a combination of rhodium and one or more other platinum metal(s) from the group comprising platinum, palladium, ruthenium and iridium, and which comprises, as promoters, one or more alkali metal hydroxides and/or alkali metal sulphates, the support of which comprises chromium and manganese.

12 Claims, No Drawings

PROCESS FOR THE PREPARATION OF HYDROOXYDIPHENYLS

BACKGROUND OF THE INVENTION

It is known that hydroxydiphenyl can be prepared in the gas phase by catalytic dehydrogenation of compounds or mixtures of compounds consisting of completely and/or partly hydrogenated hydroxydiphenyl. Dehydrogenation catalysts which comprise nickel, chromium, aluminium, copper and an alkali metal oxide or carbonate, and if appropriate silver, such as are described, for example, in German Patent Specification 1,108,221 and German Offenlegungsschrift 2,049,809, are used here.

A process for the preparation of 2-hydroxydiphenyl by dehydrogenation of cyclohexanone derivatives in the presence of a supported catalyst is known from German Offenlegungsschrift 2,211,721. The catalyst employed in this process is prepared by depositing a very small amount of palladium, platinum, iridium or rhodium or a mixture of two or more of these elements on a support, such as silica, aluminium oxide, silica/aluminium oxide or active charcoal, and by furthermore adding a suitable amount of an alkali.

In the Offenlegungsschrift mentioned, it is emphasised especially that platinum and palladium have a particularly high activity for selective formation of the desired product. However, the noble metal catalysts employed in this process have either too low a selectivity (in particular if a rhodium-containing catalyst is used), an inadequate activity or too short a life.

It is furthermore known from German Offenlegungsschrift 2,049,809 that hydroxydiphenyl can be prepared by catalytic dehydrogenation of compounds and/or mixtures of compounds, which consist of completely and/or partly hydrogenated hydroxydiphenyl in the presence of a dehydrogenation catalyst comprising nickel, chromium, aluminium, copper and an alkali. U.S. Pat. No. 4,060,559 describes a process for the preparation of 2-hydroxydiphenyl by dehydrogenation of cyclohexylphenol, in which the reaction is carried out in the presence of a supported catalyst comprising platinum or palladium. The relatively short life of the catalysts and the sometimes inadequate activity are also disadvantages of this process.

According to EP 208,933, hydroxydiphenyl can be obtained by dehydrogenation of cyclohexylidene-cyclohexanone if a Cr-Mn-Al$_2$O$_3$ catalyst comprising rhodium is used. However, the yields are in need of improvement for industrial production of hydroxydiphenyl.

SUMMARY OF THE INVENTION

The invention relates to a process for the preparation of hydroxydiphenyls by catalytic dehydrogenation in the gas phase, starting from compounds or mixtures of several compounds which consist of completely or partly hydrogenated hydroxydiphenyl, which is characterised in that a catalyst is employed which comprises, as the active constituents, a combination of rhodium and one or more platinum metal(s) from the group comprising platinum, palladium, ruthenium and iridium, and which comprises, as promoters, one or more alkali metal hydroxides and/or alkali metal sulphates, the support of which comprises chromium and manganese.

DETAILED DESCRIPTION OF THE INVENTION

The process according to the invention is accordingly characterised by the use of a catalyst which comprises a combination of rhodium and one or more platinum metal(s). Compared with a catalyst which comprises rhodium alone as the noble metal, such a catalyst has a higher stability and a longer service life, and furthermore displays an improved selectivity. Such an improvement in properties which make a large-scale industrial process economical for the first time was not to be expected. The expert also would not have considered the use of such a combination, since this is associated with the disadvantage of handling another noble metal.

Suitable starting substances for the process according to the invention are, for example, 2-cyclohexylidene-cyclohexanone, 2-cyclohexenyl-cyclohexanone, 2-cyclohexyl-cyclohexanone, 2-cyclohexyl-cyclohexanol, 2-cyclohexyl-phenol, 3-cyclohexyl-phenol, 4-cyclohexyl-phenol, 2-phenyl-cyclohexanone and 2-phenyl-cyclohexanol.

The compounds mentioned are readily accessible. Thus, for example, 2-cyclohexylidene-cyclohexanone and 2-cyclohexenyl-cyclohexanone are obtained by self-condensation of cyclohexanone in the presence of acid or basic catalysts by known methods. These two compounds furthermore are formed, in addition to 2-cyclohexyl-cyclohexanone, 2-cyclohexyl-cyclohexanol and others, as by-products in the catalytic dehydrogenation of cyclohexanol. They can be separated off from the dehydrogenation mixture easily by distillation and used as a mixture for the 2-hydroxy-diphenyl preparation.

Cyclohexyl-phenol is obtained by known methods by catalytic alkylation of phenol. 2-Cyclohexyl-phenol moreover also occurs, in addition to 2-phenyl-cyclohexanone and 2-phenyl-cyclohexanol, 2-cyclohexyl-cyclohexanol and 2-cyclohexyl-cyclohexanone, as a by-product in the synthesis of 2-hydroxydiphenyl.

The catalytic dehydrogenation of the abovementioned compounds or mixtures of compounds is in general carried out by passing the compound or mixtures of compounds in vapour form over the rhodium/platinum metal catalyst at temperatures of 300° to 400° C., preferably 320° to 390° C., under normal pressure or reduced pressure.

The total content of noble metals is 0.05 to 5% by weight, preferably 0.05 to 4% by weight, particularly preferably 0.1 to 3% by weight, based on the total weight of the catalyst. The weight content of the rhodium here is 10 to 90%, preferably 15 to 80%, particularly preferably 20 to 70%, of the total weight of the rhodium/platinum metal combination.

The other platinum metal present in addition to the rhodium is chosen from the group comprising platinum, palladium, ruthenium and iridium, preferably from the group comprising platinum, palladium and iridium, and palladium is particularly preferably chosen as the combination metal.

The catalyst to be employed furthermore comprises 1 to 12% by weight of one or more alkali metal hydroxides and/or alkali metal sulphates, the content of hydroxides and sulphates not exceeding 6% by weight of each. The content of promoters is preferably 2 to 10% by weight, the content of hydroxides and sulphates not exceeding 5% by weight of each. All the weight data relate to the weight of the finished catalyst. Suitable alkali metal hydroxides are lithium hydroxide, sodium hydroxide, potassium hydroxide, rubidium hydroxide and caesium hydroxide, preferably lithium hydroxide, sodium hydroxide and potassium hydroxide, particularly preferably sodium hydroxide and potassium hydroxide. Suitable alkali metal sulphates are lithium sulphate, sodium sulphate, potassium sulphate, rubidium sulphate and caesium sulphate, preferably lithium sulphate, sodium sulphate and potassium sulphate, particularly preferably sodium sulphate or potassium sulphate.

The constituents mentioned for the catalysts to be employed are located on a support. Examples of such supports are aluminium oxide, aluminium spinel, active charcoal, kieselguhr, bentonite, pumice, silica gel, zirconium oxide, titanium oxide, zinc oxide, magnesium oxide and oxides of the rare earths.

Aluminium oxide or an aluminium spinel is preferably employed as the catalyst support. The $\alpha$- and the $\gamma$-modification, in particular, are suitable as the aluminium oxide. Aluminium spinels are compounds of the formula Me(II)Al$_2$O$_4$ or Me(I)AlO$_2$, in which Me(II) is a divalent metal cation of iron, zinc, nickel, copper, cobalt, cadmium, magnesium or others, preferably of magnesium, and Me(I) is a monovalent cation, for example lithium (lithium-aluminium spinel). Some of the aluminium in the spinels can be replaced by trivalent iron, chromium or manganese. Preferably, however, Al$_2$O$_3$, particularly preferably $\gamma$-Al$_2$O$_3$, is employed.

The support for a catalyst which can be employed according to the invention comprises chromium and manganese in an amount of, together, 0.05 to 8% by weight, preferably 0.2 to 5% by weight, based on the total weight of the catalyst. The weight ratio of chromium and manganese is 5:1 to 1:5, preferably 2:1 to 1:2. Such supports treated with chromium and manganese are known from EP 208,933.

To prepare the catalysts described, in a particularly preferred manner a procedure can be followed in which compounds of chromium and manganese are applied to an Al$_2$O$_3$ or an aluminium spinel in the form of extruded particles, pellets or beads having dimensions of about 2 to 10 mm, the support charged in this way is heated to an elevated temperature, and the noble metals and one or more alkali metal hydroxides and/or one or more alkali metal sulphates are then applied separately; drying is carried out after each application, in general at 100° to 140° C. under reduced to normal pressure, such as 1 to 1,000 mbar, preferably 10 to 500 mbar, for example under a waterpump vacuum.

Application of the chromium and manganese to the catalyst support in the particularly preferred manner can be carried out, for example, by joint precipitation of a manganese/chromium hydroxide mixture from a chromium salt and manganese salt solution using an alkali metal hydroxide solution or ammonia, and subsequent washing out of the soluble contents with water. Possible salts of chromium and manganese are, in particular, the sulphates, chlorides, acetates and/or nitrates of the elements mentioned. The chromium and manganese can also be deposited on the catalyst support as ammonium/manganese chromate or ammonium/alkali metal/manganese chromate from a solution of manganese(II) salts and ammonium bichromate by means of ammonia and/or basic alkali metal compounds. Particularly uniform and firmly adhering deposits are obtained if the base is added slowly and uniformly, relatively large differences in concentration being avoided. For this purpose, for example, the precipitation can be carried out by means of urea under hydrolysing conditions, by which means the conditions of slow addition of the base are ensured particularly well.

After application of the compounds of chromium and manganese and the precipitation described, the catalyst support charged in this way is washed free from soluble compounds, before it is heated to elevated temperatures (about 200° to 450° C., preferably 250° to 350° C.). After this heat treatment, the support charged with chromium and manganese is ready for impregnation with the other catalyst constituents mentioned.

The impregnation of the support with the noble metals and with the alkali metal hydroxide and/or alkali metal sulphate (in each case one or more of these) is carried out separately. A procedure can be followed here in which the noble metals are first impregnated onto the support, for example in the form of aqueous solutions of their chlorides, nitrates, acetates or other suitable salts, further impregnation with an alkali metal hydroxide solution being carried out after drying. In this treatment, the noble metals are precipitated in the form of their oxides or hydroxides. Impregnation of the alkali metal hydroxides onto the support can be carried out separately or together with the impregnation of an alkali metal sulphate onto the support. After final drying, the catalyst is available for use. Before being used, it is preferably activated by treatment with hydrogen at an elevated temperature, for example at 120° to 400° C., preferably at 150° to 380° C. This activation is particularly preferably carried out in the reactor in which the preparation of the hydroxydiphenyl is later carried out.

However, it is also possible first to impregnate the support with an alkali metal hydroxide solution, and then to dry it and to apply the above salts of the noble metals onto the catalyst support which has been pretreated in this way and rendered basic, precipitation of the noble metals in the form of their oxides or hydroxides also taking place at the time of impregnation. In this variant, additional impregnation of one or more alkali metal sulphates onto the support, together with the alkali metal hydroxide, can be carried out before or after application of the alkali metal hydroxide or as a final impregnation after application of the noble metals. Here also, separate drying is carried out after each impregnation. According to this variant, the catalyst is also ready to use after subsequent drying, but can be activated beforehand with hydrogen at an elevated temperature in the manner described.

Instead of impregnating the support mentioned in order to charge it with the substances mentioned, it can also be sprayed with suitable solutions. The working apparatuses necessary for this and the adjustment of the desired charging by choosing the amount and concentration of the solutions of the elements mentioned are known in principle to the expert.

In addition to aqueous solutions, alcoholic solutions or solutions in lower carboxylic acids or lower amines in principle are also possible, if the envisaged salts of the noble metals and the basic alkali metal compounds are soluble therein.

EXAMPLES

Example 1

A solution of 41.5 g of MnSO$_4$.H$_2$O, 30.9 g of (NH$_4$)$_2$Cr$_2$O$_7$ and 225 9 of urea in 359 g of water was added to 500 g of spherical Al$_2$O$_3$ (diameter 4 to 6 mm)

having a BET surface area of 300 m²/g in a round-bottomed flask. The flask was kept at 85° C. for one hour, under a rotary movement, the liquid which had not been absorbed was filtered off, and the catalyst support was washed free from sulphate with water and dried at 120° C. under a waterpump vacuum for 20 hours. The catalyst support was then conditioned at 300° C. for 30 minutes. 50 g of an Al$_2$O$_3$ charged with chromium and manganese in this way were impregnated with a solution which consisted of 0.66 g of RhCl$_3$ and 0.83 g of H$_2$PtCl$_6$ in 20 ml of water. The moist catalyst pellets were dried at 120° C. under a waterpump vacuum, and then impregnated again with a solution of 1.46 g of NaOH in 15 ml of water and dried again. Finally, the pellets were impregnated again with a solution of 1.5 g of K$_2$SO$_4$ in 15 ml of water and dried again. A reaction tube having a diameter of 17 mm and a length of about 600 mm, the upper part of which served as an evaporation zone and which was filled with 30 ml (23.5 g) of the prepared catalyst in the lower section, was kept at 400° C. for 70 hours by electrical heating, while 10 l of N$_2$/hour were passed over the catalyst. The catalyst was then activated at this temperature in a stream of H$_2$ (10 l of H$_2$/hour) for 71 hours. Using a calibrated metering device, 6 g of a mixture of 2-cyclohexenyl-cyclohexanone and 2-cyclohexylidene-cyclohexanone together with 10 l of hydrogen were passed into the reaction tube per hour. The liquid starting mixture evaporated in the upper part of the tube, which contained only packing.

During the first 24 hours of operation, the catalyst was kept at 375° C. A reaction product which had the following composition was formed during this period:

| | |
|---|---|
| 2-hydroxy-diphenyl | 90.7% |
| diphenylene oxide | 3.4% |
| diphenyl | 0.6% |
| phenol | 0.4% |
| 2-cyclohexyl-phenol | 4.5% |

After this start-up time, the temperature in the reaction oven was set at 350° to 375° C. The reaction product had the following composition (% by weight), depending on the duration of use of the catalyst:

| Substances (%)/time (hours) | 146 | 797 | 1239 | 2188 | 3023 | 5078 |
|---|---|---|---|---|---|---|
| 2-Hydroxy-diphenyl | 92.9 | 91.1 | 89.8 | 90.2 | 90.3 | 90.6 |
| 2-Cyclohexyl-phenol | 1.5 | 0.7 | 0.7 | 1.2 | 2.2 | 1.4 |
| Diphenylene oxide | 4.0 | 5.5 | 6.2 | 5.8 | 5.3 | 4.9 |
| Diphenyl | 0.7 | 0.9 | 1.2 | 1.0 | 0.8 | 1.3 |
| Phenol | 0.3 | 0.3 | 0.3 | 0.2 | 0.3 | 0.1 |

2-Cyclohexyl-phenol can be employed again as starting material in the reaction.

Example 2

200 g of a Cr-Mn-Al$_2$O$_3$ catalyst support prepared according to Example 1 was impregnated with a solution which had been prepared from 2.64 g of RhCl$_5$, 2.12 g of palladium acetate and 80 g of water. The moist catalyst beads were dried at 120° C. under a waterpump vacuum. 30 g of the dried catalyst were impregnated with a solution of 1.29 g of KOH and 0.9 g of K$_2$SO$_4$ in 10 g of water, and were then dried again. 30 ml (23.1 g) of the catalyst prepared in this way were heated to 400° C. in a stream of hydrogen (10 l/hour), using the reaction tube described in Example 1, and were kept at this temperature for 65 hours. The oven temperature was then reduced and the dehydrogenation reaction was carried out at 350° and 380° C.

The following results were obtained in the dehydrogenation of the isomer mixture of 2-cyclohexenyl-cyclohexanone and 2-cyclohexylidene-cyclohexanone at a catalyst loading of 0.2 g/ml.hour and 0.4 g/ml.hour at 350° and 380° C. respectively:

a) at 350° C. and a loading of 0.2 g/ml/hour

| Substances (%)/time (hours) | 460 | 1048 | 2086 |
|---|---|---|---|
| 2-Hydroxy-diphenyl | 84.2 | 89.7 | 90.5 |
| 2-Cyclohexyl-phenol | 11.2 | 4.7 | 3.7 |
| Diphenyl | 0.3 | 0.5 | 0.4 |
| Diphenylene oxide | 2.8 | 3.7 | 4.0 |
| Phenol | 0.6 | 0.4 | 0.4 | b) subsequently at 380° C. and a loading of 0.4 g/ml/hour; the operating hours (time) were counted further.

| Substances (%)/time (hours) | 3117 | 4130 | 7122 | 7314 | 7407 |
|---|---|---|---|---|---|
| 2-Hydroxy-diphenyl | 88.6 | 86.2 | 90.0 | 92.8 | 91.3 |
| 2-Cyclohexyl-phenol | 6.2 | 8.2 | 4.5 | 2.3 | 3.1 |
| Diphenyl | 0.2 | 0.2 | 0.4 | 0.3 | 0.3 |
| Diphenylene oxide | 4.0 | 4.0 | 3.4 | 4.7 | 4.5 |
| Phenol | 0.1 | 0.2 | 0.2 | 0.2 | — |

After 4,674 operating hours, the catalyst was regenerated by being conditioned at 345° to 410° C. in a stream of air (20 l/hour) for 16 hours, and was then activated in a stream of hydrogen (10 l/hour) at 400° C. for 70 hours.

Example 3

The catalyst preparation according to Example 1 was repeated, with the exception that a spherical Al$_2$O$_3$ (diameter 2 to 4 mm) having a specific surface area of 80 m²/g was employed to prepare the catalyst support.

30 ml (21 g) of this catalyst were first activated in a stream of hydrogen (10 l/hour) at 400° C. for 69 hours in the same apparatus as in Example 1. The dehydrogenation of dianone (condensation product of 2 molecules of cyclohexanone, isomer mixture) was then carried out using 10 l of hydrogen/hour as the carrier gas and at a temperature of the reaction oven of 350° to 380° C. The reaction product showed the following composition as a function of time (operating hours of the catalyst):

| Substances (%)/time (hours) | 47 | 864 | 2132 | 2245 | 2892 | 3978 | 4448 | 5645 |
|---|---|---|---|---|---|---|---|---|
| 2-Hydroxy-diphenyl | 91.9 | 91.2 | 85.1 | 87.6 | 90.6 | 89.0 | 88.8 | 83.6 |
| 2-Cyclohexyl-phenol | 1.3 | 0.7 | 9.2 | — | — | 3.4 | 4.7 | 11.6 |
| Diphenylene oxide | 3.3 | 4.1 | 2.3 | 5.4 | 4.4 | 3.9 | 3.2 | 2.5 |
| Diphenyl | 1.9 | 2.1 | 1.0 | 3.7 | 2.7 | 2.1 | 2.1 | 0.6 |
| Phenol | 0.2 | 0.2 | 0.2 | 0.2 | 0.1 | 0.1 | — | 0.1 |
| Loading (g/ml/hour) | 0.2 | 0.2 | 0.38 | 0.2 | 0.2 | 0.2 | 0.2 | 0.41 |

After 2,132 operating hours, the catalyst was regenerated by being conditioned at 375° to 405° C. in a stream of air (8 to 20 l/hour) for 20 hours, and was then activated again in a stream of hydrogen (10 l/hour) at 400° C. for 74 hours.

What is claimed is:

1. A process for the preparation of hydroxydiphenyl, which comprises dehydrogenating, at a temperature of from 300° C. to 400° C. and at atmospheric or reduced pressure, one or more compounds selected from the group consisting of completely hydrogenated hydroxydiphenyls, and partially hydrogenated hydroxydiphenyls, in the gas phase in the presence of a catalyst comprising a combination of rhodium, with one or more platinum metals selected from the group consisting of platinum, palladium, ruthenium and iridium, said catalyst also comprising a promotor selected from the group consisting of one or more alkali metal hydroxides, alkali metal sulphates and mixtures thereof and being supported on a support comprising chromium and manganese.

2. The process of claim 1, wherein only one other platinum metal is present in addition to rhodium.

3. The process of claim 1, wherein the platinum metal(s) is or are selected from the group comprising platinum, palladium and iridium.

4. The process of claim 3, wherein the platinum metal is palladium.

5. The process of claim 1, wherein said combination of rhodium, with one or more platinum metals are present in a total amount of 0.05 to 5% by weight, based on the total weight of the catalyst.

6. The process of claim 5, wherein said combination of rhodium, with one or more platinum metals are present in a total amount of 0.05 to 4% by weight, based on the total weight of the catalyst.

7. The process of claim 6, wherein said combination of rhodium, with one or more platinum metals are present in a total amount of 0.1 to 3% by weight, based on the total weight of the catalyst.

8. The process of claim 1, wherein the weight content of the rhodium is 10 to 90% of the total weight of the rhodium/platinum metal combination.

9. The process of claim 8, wherein the weight content of the rhodium in the combination is 15 to 80%.

10. The process of claim 9, wherein the weight content of the rhodium in the combination is 20 to 70%.

11. The process of claim 1, wherein said promotor is present in an amount of 1 to 12%, and the amount of said alkali metal hydroxide and the amount of said alkali metal sulphate does not exceed 6% by weight of each, based on the total weight of the catalyst.

12. The process of claim 1, wherein the support comprising chromium and manganese is $Al_2O_3$.

* * * * *